US 11,730,896 B2

(12) United States Patent
Hutchins, IV et al.

(10) Patent No.: US 11,730,896 B2
(45) Date of Patent: Aug. 22, 2023

(54) MULTISTAGE VAPORIZER FOR MEDICAL TREATMENT SYSTEM

(71) Applicant: Vaporox, Inc., Denver, CO (US)

(72) Inventors: Loren Havener Hutchins, IV, Parker, CO (US); Wesley Joseph Weber, Golden, CO (US)

(73) Assignee: VAPOROX, INC., Denver, CO (US)

(*) Notice: Subject to any disclaimer, the term of this patent is extended or adjusted under 35 U.S.C. 154(b) by 0 days.

(21) Appl. No.: 17/813,482

(22) Filed: Jul. 19, 2022

(65) Prior Publication Data
US 2022/0347400 A1 Nov. 3, 2022

Related U.S. Application Data

(63) Continuation of application No. PCT/US2021/059481, filed on Nov. 16, 2021.

(60) Provisional application No. 63/114,256, filed on Nov. 16, 2020.

(51) Int. Cl.
*A61M 11/00* (2006.01)
*A61M 35/00* (2006.01)

(52) U.S. Cl.
CPC .......... *A61M 11/005* (2013.01); *A61M 35/20* (2019.05); *A61M 35/30* (2019.05)

(58) Field of Classification Search
CPC ..... A61M 11/005; A61M 35/20; A61M 35/30
USPC ........................................................ 604/289
See application file for complete search history.

(56) References Cited

U.S. PATENT DOCUMENTS

| | | | |
|---|---|---|---|
| 3,101,716 A | 8/1963 | Cornell, Jr. | |
| 3,744,491 A | 7/1973 | Fischer | |
| 4,236,513 A | 12/1980 | LoPiano | |
| 4,331,137 A | 5/1982 | Sarui | |
| 4,432,354 A | 2/1984 | Lasley | |
| 4,670,010 A | 6/1987 | Dragone | |
| 4,772,259 A | 9/1988 | Frech et al. | |
| 5,098,415 A | 3/1992 | Levin | |

(Continued)

FOREIGN PATENT DOCUMENTS

| | | |
|---|---|---|
| CA | 2032263 A1 | 1/1990 |
| CA | 2 528 965 | 11/2004 |

(Continued)

OTHER PUBLICATIONS

International Search Report dated May 8, 2008, issued in International Appl. No. PCT/US06/28799.

(Continued)

*Primary Examiner* — Andrew J Mensh
(74) *Attorney, Agent, or Firm* — Knobbe Martens Olson & Bear LLP

(57) ABSTRACT

Multistage vaporizers, such as for use in medical treatment systems, as well as related methods are described. In one example, a multistage vaporizer includes a first reservoir configured to hold a liquid and one or more pumping transducers positioned in the first reservoir. The multistage vaporizer also includes a second reservoir and one or more vaporizing transducers positioned in the second reservoir. The one or more pumping transducers positioned in the first reservoir are configured to generate and move droplets of a liquid in the first reservoir to the second reservoir, and the one or more vaporizing transducers positioned in the second reservoir are configured to create a vapor of the liquid in the second reservoir.

18 Claims, 12 Drawing Sheets

(56) References Cited

U.S. PATENT DOCUMENTS

| | | | |
|---|---|---|---|
| 5,188,099 A | 2/1993 | Todeschini | |
| 5,228,431 A | 7/1993 | Giarretto | |
| 5,312,385 A | 5/1994 | Greco | |
| 5,447,504 A | 9/1995 | Baker et al. | |
| 5,848,998 A | 12/1998 | Marasco, Jr. | |
| 6,273,906 B1 | 8/2001 | Swanson | |
| 6,443,978 B1 | 9/2002 | Zharov | |
| 6,868,851 B2 | 3/2005 | Heinonen | |
| 7,665,460 B2 | 2/2010 | Lindsay et al. | |
| 7,771,402 B2 | 8/2010 | Marasco | |
| 7,934,703 B2 * | 5/2011 | Tomono | B05B 7/0012 261/DIG. 65 |
| 8,048,044 B2 | 11/2011 | Stryker et al. | |
| 8,241,258 B2 | 8/2012 | Pelkus | |
| 8,353,882 B1 | 1/2013 | Pelkus | |
| 8,499,764 B2 | 8/2013 | Hills et al. | |
| 11,090,475 B2 | 8/2021 | Pelkus | |
| 2003/0023283 A1 | 1/2003 | McDaniel | |
| 2004/0260253 A1 | 12/2004 | Rosati | |
| 2005/0107766 A1 | 5/2005 | Ott et al. | |
| 2006/0069357 A1 * | 3/2006 | Marasco | A61M 1/92 604/289 |
| 2007/0286809 A1 | 12/2007 | Williams et al. | |
| 2008/0091179 A1 | 4/2008 | Durkin et al. | |
| 2009/0048555 A1 | 2/2009 | Stryker et al. | |
| 2009/0112170 A1 | 4/2009 | Wells | |
| 2009/0234270 A1 | 9/2009 | Loebel et al. | |
| 2010/0001096 A1 * | 1/2010 | Lu | B05B 7/0012 239/102.2 |
| 2010/0022941 A1 | 1/2010 | Pelkus | |
| 2010/0150991 A1 | 6/2010 | Bernstein | |
| 2010/0219263 A1 | 9/2010 | Feriani et al. | |
| 2011/0061479 A1 | 5/2011 | Burt et al. | |
| 2012/0022436 A1 | 1/2012 | Bradley | |
| 2012/0071813 A1 | 3/2012 | Schaefer | |
| 2012/0138050 A1 | 6/2012 | Wondka et al. | |
| 2012/0302976 A1 | 11/2012 | Locke et al. | |
| 2016/0256637 A1 * | 9/2016 | Kern | A61M 15/0085 |
| 2016/0354559 A1 * | 12/2016 | Gavini | A61M 15/0085 |
| 2017/0232211 A1 | 8/2017 | Gallem et al. | |
| 2017/0361345 A1 | 12/2017 | Maeda et al. | |
| 2017/0368270 A1 | 12/2017 | Kinoshita et al. | |
| 2018/0066645 A1 | 3/2018 | Mazur | |
| 2018/0110939 A1 | 4/2018 | Lanzkowsky | |
| 2020/0101241 A1 | 4/2020 | Pelkus | |

FOREIGN PATENT DOCUMENTS

| | | |
|---|---|---|
| CN | 1788709 A | 6/2006 |
| CN | 201171784 Y | 12/2008 |
| WO | WO 2008/013524 A2 | 1/2008 |
| WO | WO 2014/092802 | 6/2014 |

OTHER PUBLICATIONS

Extended/Supplementary European Search Report for EP Application No. 13861708.9 dated May 2, 2017.

International Search Report for International Application No. PCT/US2013/048801 dated Jan. 31, 2014.

International Search Report for International Application No. PCT/US15/18856 dated May 27, 2015.

Supplementary European Search Report for Application No. EP 15 76 4163 dated Jan. 17, 2018.

Office Action received in related Chinese Application No. 201580027022.X dated Apr. 1, 2019.

International Search Report for International Application No. PCT/US21/59481 dated Feb. 3, 2022.

* cited by examiner

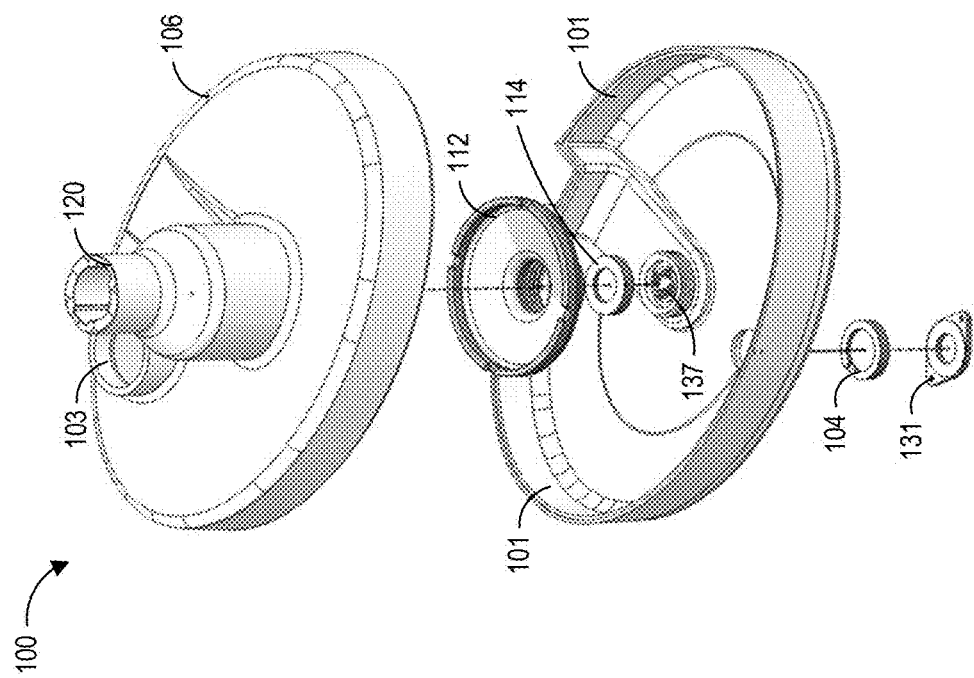
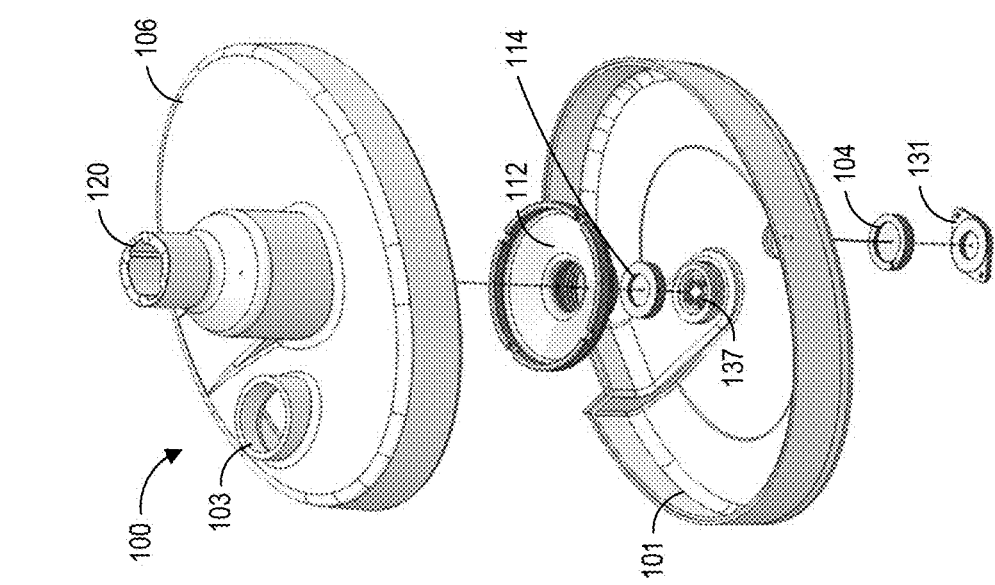
FIG. 2D
FIG. 2C

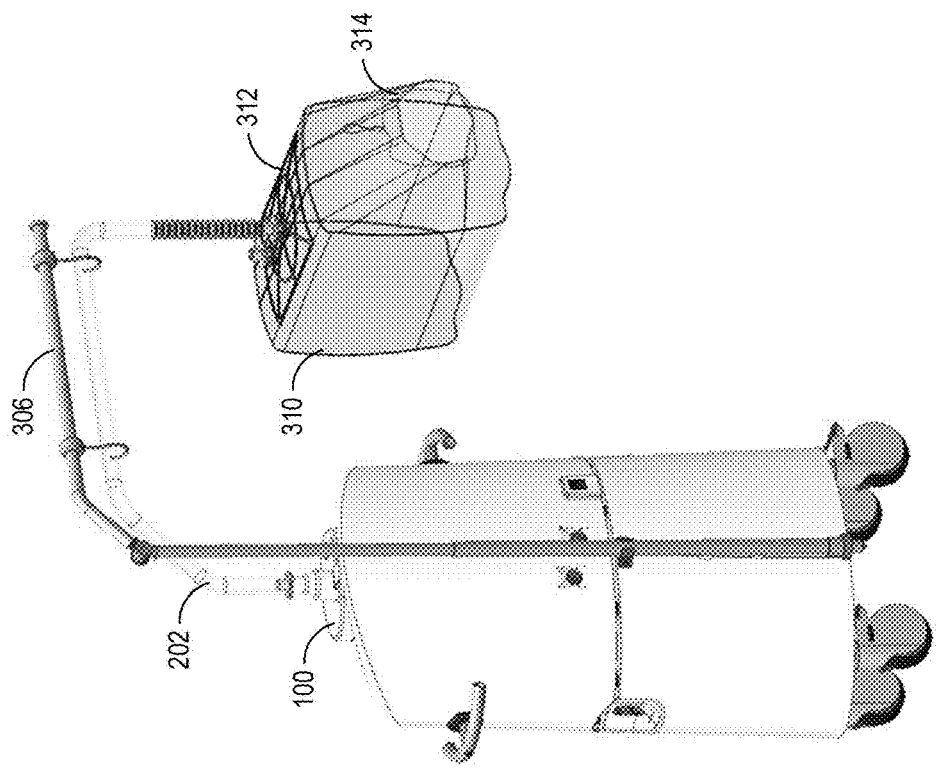
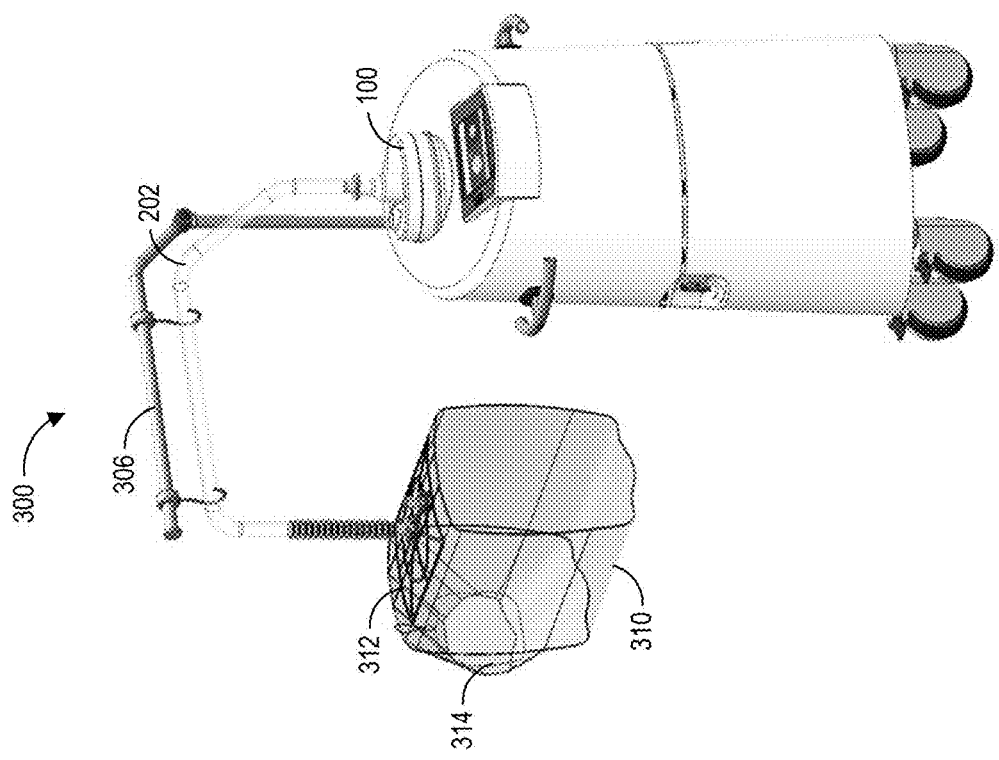
FIG. 5B
FIG. 5A

MULTISTAGE VAPORIZER FOR MEDICAL TREATMENT SYSTEM

PRIORITY APPLICATION

This application is a continuation of PCT/US2021/059481, filed on Nov. 16, 2021, which claims priority to U.S. Provisional Patent Application No. 63/114,256, Nov. 16, 2020, each of which are incorporated herein by reference. Any and all applications for which a foreign or domestic priority claim is identified in the Application Data Sheet as filed with the present application are hereby incorporated by reference under 37 CFR 1.57.

BACKGROUND

This application relates to vaporizers configured to generate a mist from a liquid. In some embodiments, this application relates to a multistage vaporizer that can be used in a medical treatment system.

SUMMARY

Multistage vaporizers are disclosed that are configured to generate a mist or vapor of vaporized liquid (e.g., a spray, an aerosol, a suspension of liquid droplets or particles in a gas, etc.). In some embodiments, the multistage vaporizers produce a mist of consistent droplet size. In some embodiments, the vaporizers described herein can utilize two sets of vibrating transducers (such as piezoelectric or ultrasonic transducers comprising vibrating diaphragms, also referred to herein as crystals) in a multistage arrangement.

In a first stage, one or more "pumping" transducers can be provided in a first reservoir filled with a liquid. The pumping transducers can be configured to "throw" or otherwise generate or move relatively large droplets (large relative to the size of the vaporized droplets produced in a second stage described below) or a stream of the liquid upward, where the droplets or stream are collected on a sloped surfaced positioned above the first reservoir. The sloped surface is configured to direct the droplets to a second reservoir. In some embodiments, the pumping transducers move liquid directly into the second reservoir, for example, without being collected on the sloped surface. In the second stage, one or more "vaporizing" transducers can be provided that are configured to vaporize the liquid in the second reservoir into a fine mist, for example, of consistently sized droplets. The vaporizers described herein are considered "multistage" because they use two sets of transducers in two stages: first, as a pump to move liquid from the first reservoir to the second reservoir, and second, to vaporize the liquid.

Further, to produce the fine mist (e.g., of consistently sized droplets), it can be important to maintain a consistent fluid height in the second reservoir where vaporization occurs. In some embodiments, the multistage vaporizers described herein can maintain a consistent fluid height in the second reservoir through the use of a wall that contains the liquid in the second reservoir and that includes a cleft or other opening at a specific height. The second reservoir can fill with liquid to the lowest level of the cleft, which allows an any additional liquid to spill out, maintaining a consistent fluid height in the second reservoir. In some embodiments, excess liquid that spills through the cleft is directed back to the first reservoir.

Additionally, in some embodiments, a mote wall may be included that extends downwardly from the sloped surface into the second reservoir. The mote wall can separate the second reservoir into an inner portion in which the vaporizing transducer is positioned and an outer portion at which droplets collected on the sloped surface or droplets or a stream generated by the pumping transducer fall into the second reservoir. The mote wall can reduce ripples, wakes, or other surface disturbances caused by the falling droplets or stream and create a smooth liquid surface within the inner portion of the second reservoir, improving the quality of the fine mist of consistently sized droplets.

The multistage vaporizers can be integrated into medical systems configured for treatment using a mist of vaporized water and/or medicament. In some embodiments, the medical systems are configured for treatment of wounds, such as diabetic foot ulcers, among others.

In one aspect, a multistage vaporizer includes a first reservoir configured to hold a liquid; one or more pumping transducers positioned in the first reservoir; a second reservoir; one or more vaporizing transducers positioned in the second reservoir, wherein: the one or more pumping transducers positioned in the first reservoir are configured to generate and move droplets of a liquid in the first reservoir to the second reservoir, and the one or more vaporizing transducers positioned in the second reservoir are configured to create a vapor of the liquid in the second reservoir.

The multistage vaporizer can include one or more of the following features in any combination: (a) wherein the one or more pumping transducers and the one or more vaporizing transducers comprise piezoelectric or ultrasonic transducers comprising vibrating diaphragms; (b) a top cover positioned over the first reservoir and having a sloped surface, wherein the one or more one or more pumping transducers are configured to generate the droplets of the liquid up to the sloped surface of the top cover, and wherein the sloped surface directs the droplets of the liquid to the second reservoir; (c) wherein the sloped surface collects the droplets of the liquid and based on surface tension deposits the droplets in the second reservoir; (d) wherein the second reservoir comprises a wall having a specific height; (e) wherein the wall includes a cleft to maintain a constant volume of liquid within the second reservoir; (g) wherein the one or more vaporizing transducers and the specific height of the liquid allows for sensing of the liquid to determine fluid density and uses this with a formula/lookup table to further control vaporization; (h) a mote wall extending downwardly from the sloped surface into the second reservoir and configured to reduce surface wake over the vaporizing transducer; and/or other features as described herein.

In another aspect, a medical treatment system can include a multistage vaporizer as described above or herein, and a treatment chamber adapted to receive a portion of a body of patient, wherein vapor generated by the multistage vaporizer is directed into the treatment chamber. The medical treatment system can include one or more of the following features in any combination: (a) wherein the treatment chamber is adapted to receive at least a foot of the patient therein; (b) wherein the treatment chamber is disposable; and/or other features as described herein.

In another aspect, a method can include generating and moving droplets of a liquid from a first reservoir to a second reservoir using one or more pumping transducers positioned in the first reservoir, and generating a vapor of the liquid in the second reservoir using one or more vaporizing transducers positioned in the second reservoir.

The method can include one or more of the following features in any combination: (a) wherein the one or more pumping transducers and the one or more vaporizing transducers comprise piezoelectric or ultrasonic transducers comprising vibrating diaphragms; (b) wherein generating and moving droplets of a liquid from a first reservoir to a second reservoir using one or more pumping transducers positioned in the first reservoir comprises vibrating the one or more pumping transducers at a first frequency; (c) wherein generating a vapor of the liquid in the second reservoir using one or more vaporizing transducers positioned in the second reservoir comprises vibrating the one or more vaporizing transducers at a second frequency, wherein the second frequency is different than the first frequency; (d) wherein moving droplets of a liquid from the first reservoir to the second reservoir comprises collecting the droplets on a sloped surface which directs the droplets to the second reservoir; (e) using the one or more vaporizing transducers and a specific height of the liquid allows to determine a fluid density of the liquid; (f) selecting one or more vaporization parameters based on the fluid density and a formula/lookup table to further control vaporization; (g) directing the vapor into a treatment chamber, wherein the treatment chamber is adapted to receive a portion of a body of a patient; (h) wherein the treatment chamber is adapted to receive at least a foot of the patient therein; and/or other features as described herein.

BRIEF DESCRIPTION OF THE DRAWINGS

The features and advantages of the multistage vaporizer devices and related systems and methods described herein will become apparent from the following description, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings may not be drawn to scale.

FIGS. 2A-2D are various exploded perspective views of the multistage vaporizer of FIG. 1A.

FIGS. 5A and 5B are front and back perspective views of an embodiment of a medical treatment system including the multistage vaporizer of FIG. 1A.

DETAILED DESCRIPTION

The features of the multistage vaporizer devices and related systems and methods described herein will become more fully apparent from the following description of specific embodiments illustrated in the figures. These embodiments are intended to illustrate the principles of this disclosure, and this disclosure should not be limited to merely the illustrated examples. The features of illustrated embodiments can be modified, combined, removed, and/or substituted as will be apparent to those of ordinary skill in the art upon consideration of the principles disclosed herein.

Figure 1A:
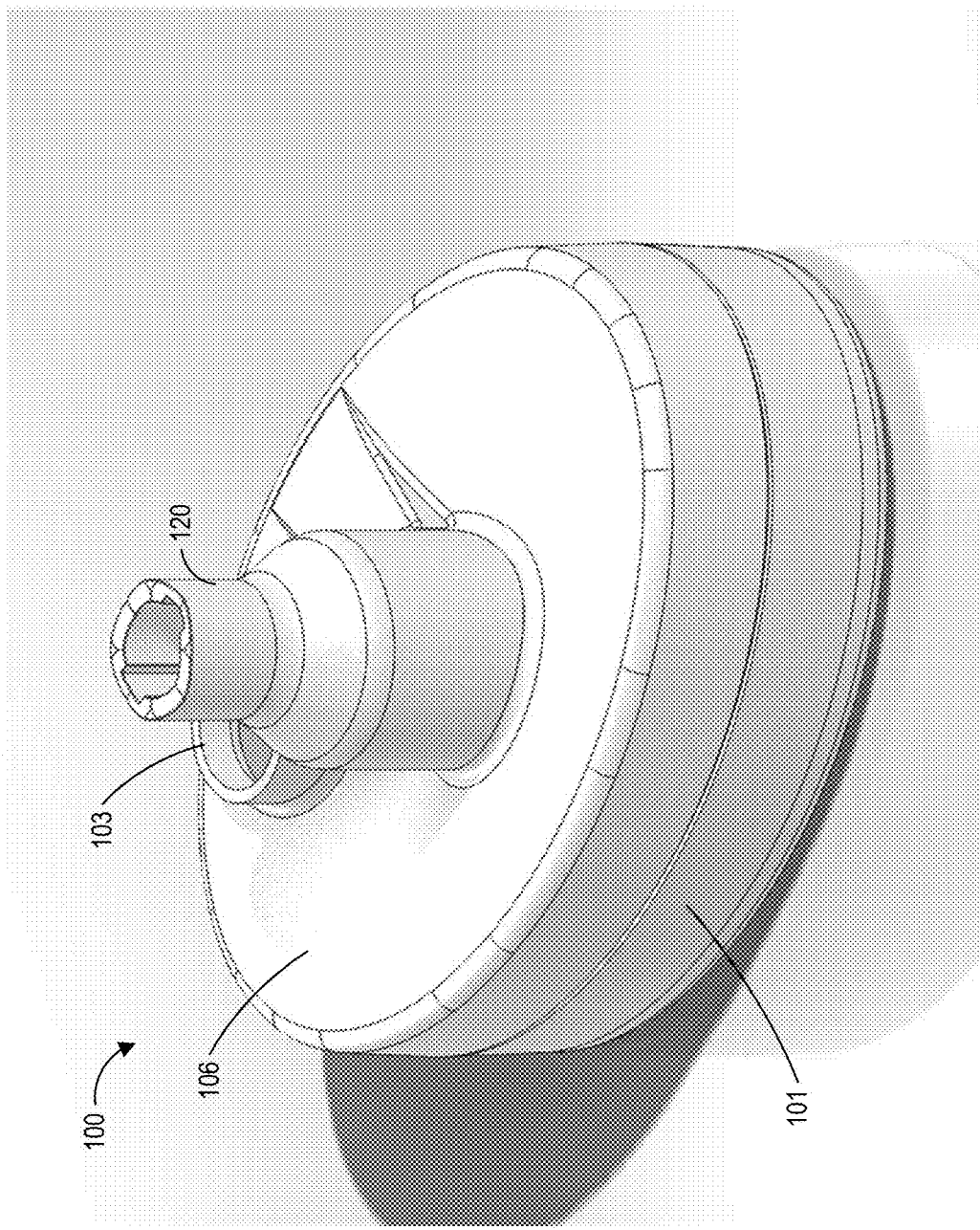
FIG. 1A is a perspective view of an embodiment of a multistage vaporizer.
Figure 1B:
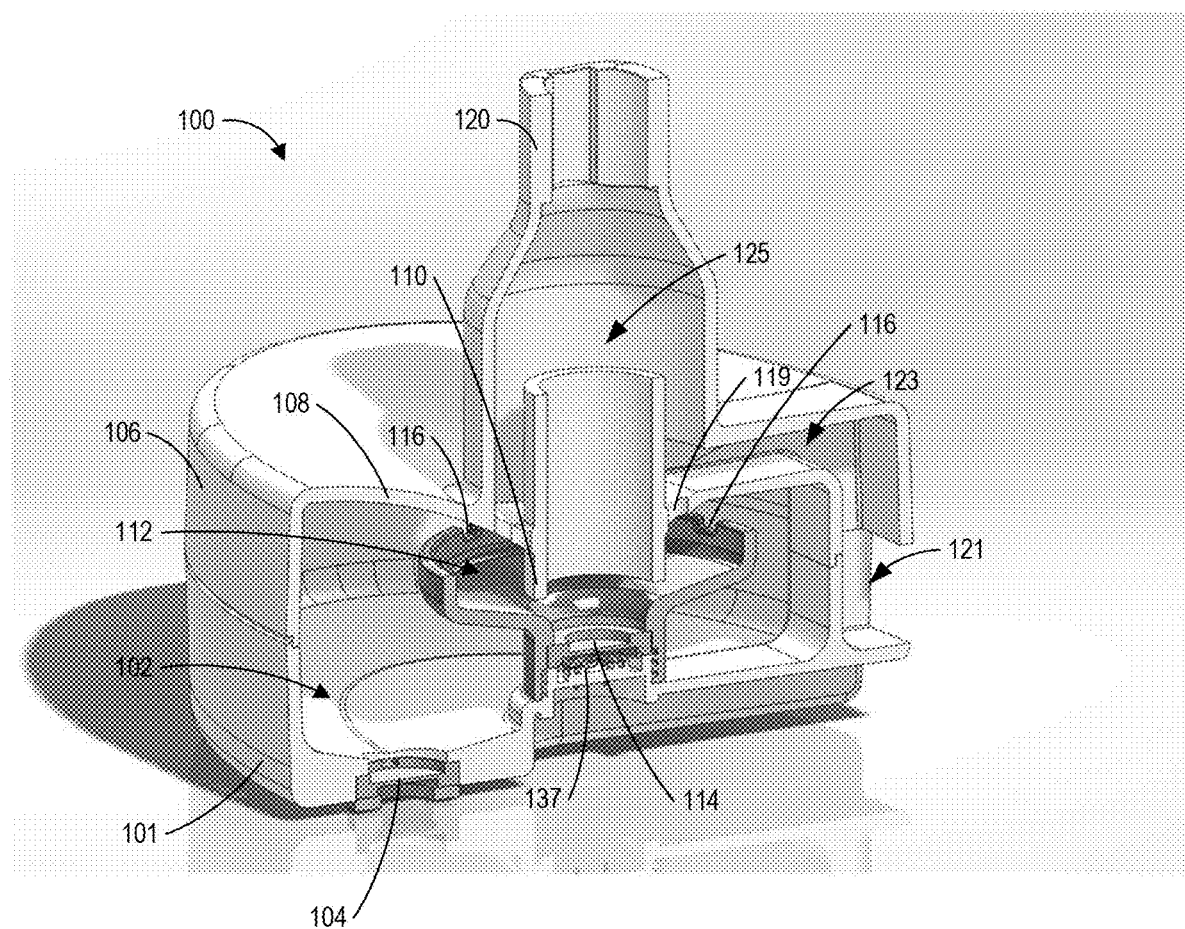
FIG. 1B is a perspective cross-sectional view of the multistage vaporizer of FIG. 1A.
Figure 1C:
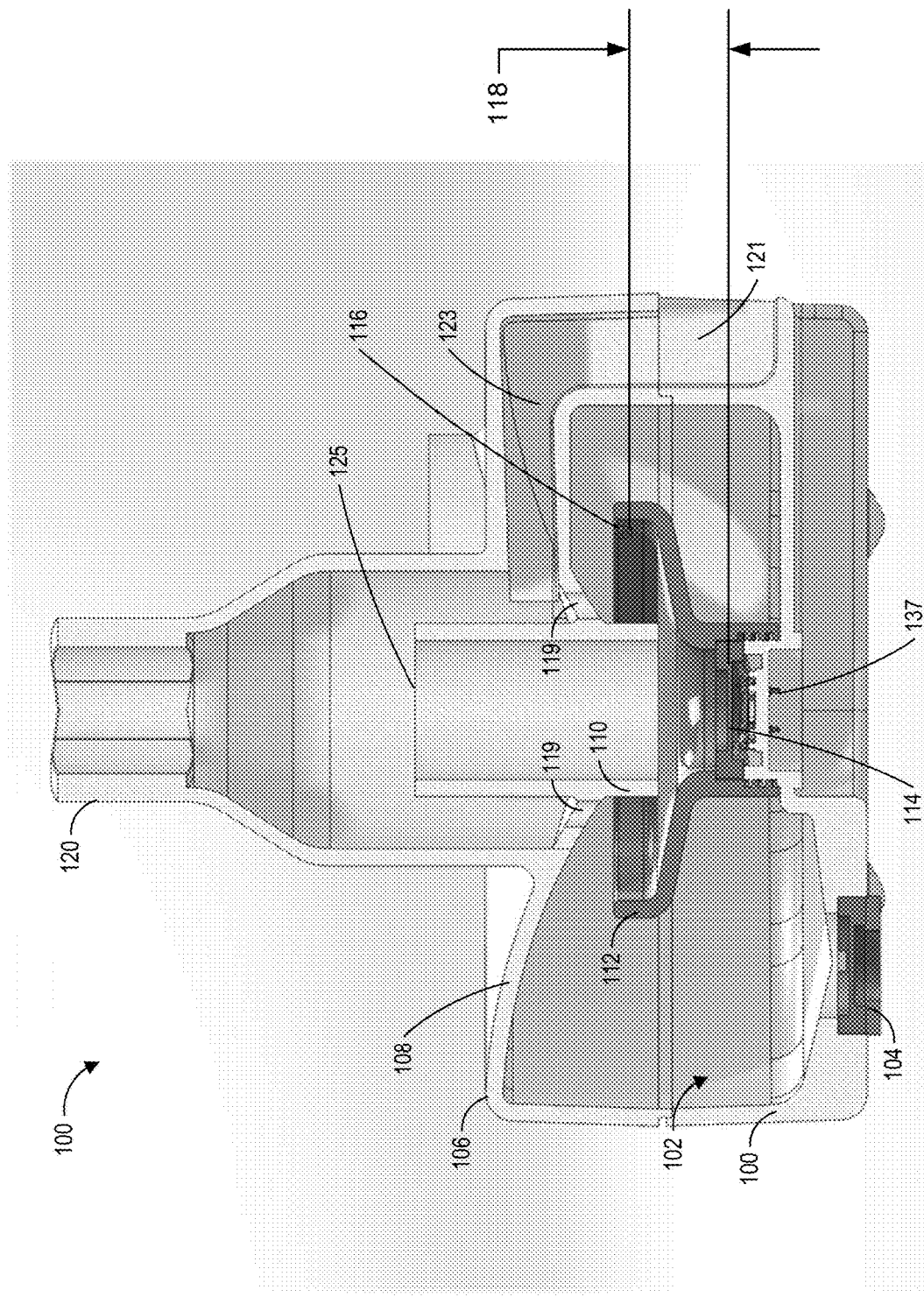
FIG. 1C is another cross-sectional view of the multistage vaporizer of FIG. 1A.
Figure 2B:
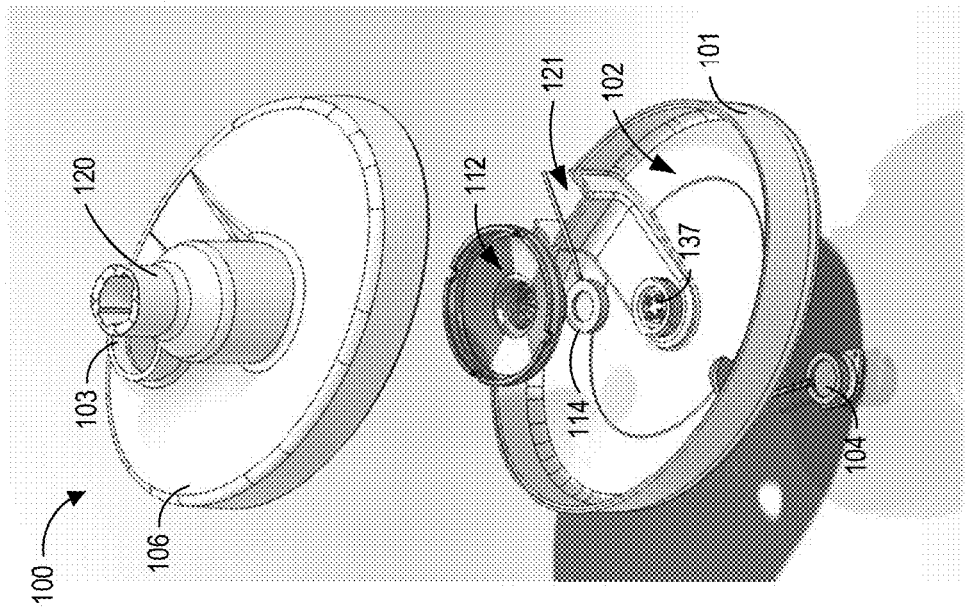
Figure 2A:
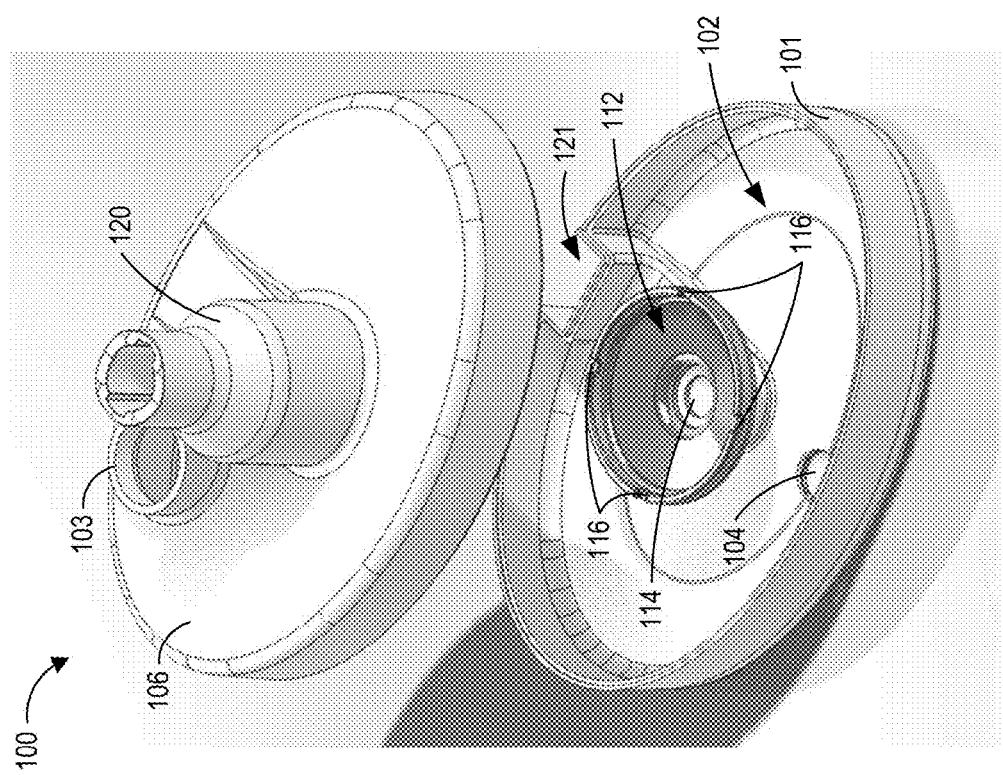
Figure 2E:
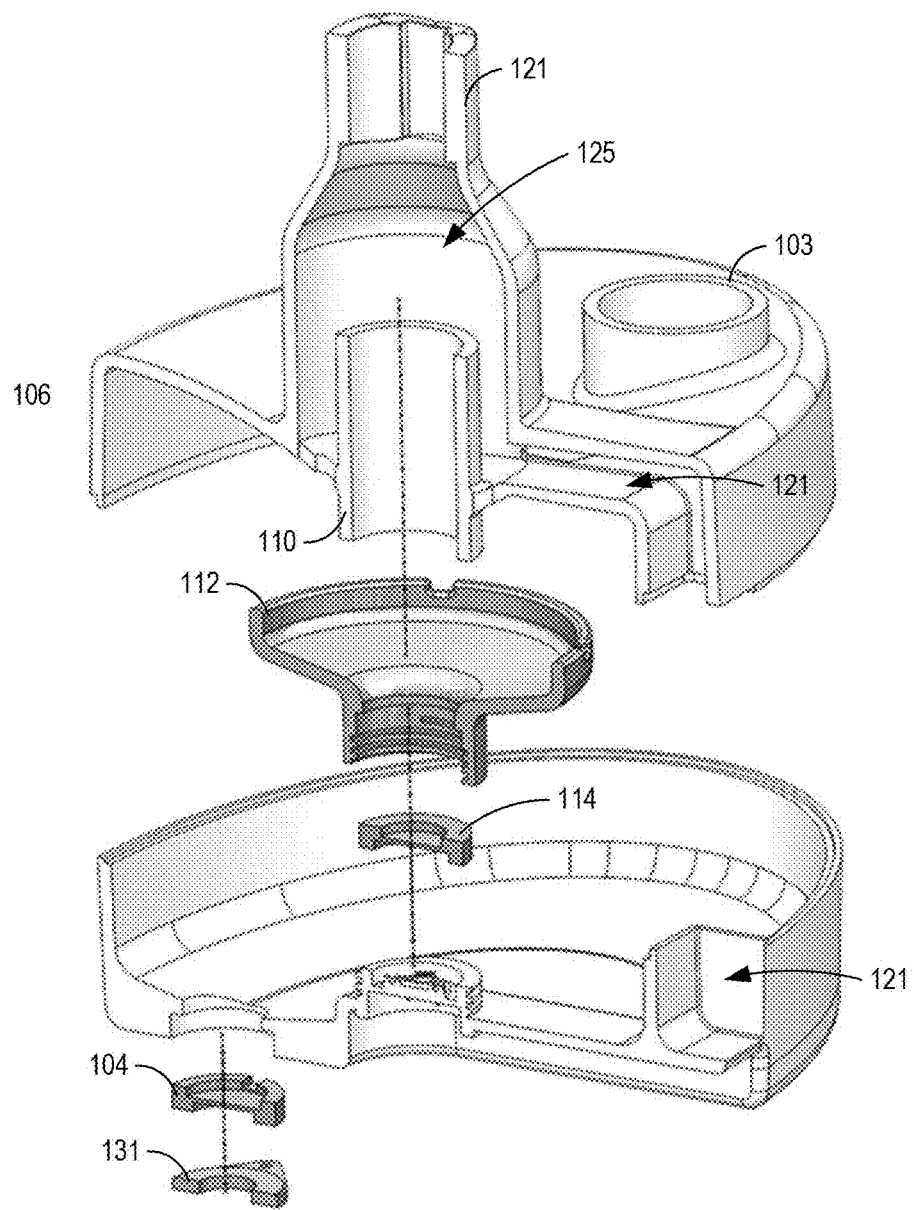
FIG. 2E is an exploded, cross-sectional, perspective view of the multistage vaporizer of FIG. 1A.

FIGS. 1A-2E illustrate various views of an embodiment of a multistage vaporizer 100. FIG. 1A is a perspective view, FIG. 1B is a perspective cross-sectional view, and FIG. 1C is another cross-sectional view of the multistage vaporizer 100. FIGS. 2A-2D are various exploded perspective views, and FIG. 2E is an exploded, cross-sectional, perspective view of the multistage vaporizer 100.

As shown in FIG. 1A, the multistage vaporizer 100 comprises a base 101 and a cover 106. FIG. 1A illustrates the multistage vaporizer 100 with the cover 106 installed on the base 101. In this assembled configuration, the base 101 and cover 106 define or enclose an interior region. Within the interior region, the multistage vaporizer 100 can include various components configured to generate a mist from a liquid. The interior region and components thereof are illustrated in FIGS. 1B-2E, which are described in detail below.

As shown in FIG. 1A, the multistage vaporizer 100 can include a fill port 103. The fill port 103 can allow a liquid to be vaporized to be introduced into the interior region of the multistage vaporizer 100. In the illustrated embodiment, the fill port 103 is included on the cover 106. FIG. 1A also illustrates that the multistage vaporizer 100 includes a vapor exhaust 120. The vapor exhaust 120 can allow a mist or vapor generated from the liquid to exit the multistage vaporizer 100. In the illustrated embodiment, the vapor exhaust 120 is included on the cover 106.

Turning to FIGS. 1B-1C, which illustrate cross-sectional views of the multistage vaporizer 100 to visualize the interior region, the multistage vaporizer 100 includes a first reservoir 102 with a pumping transducer 104 positioned therein, the cover 106, and a second reservoir 112 with a vaporizing transducer 114 positioned therein. The multistage vaporizer 100 is referred to as "multistage" because it uses the transducers 104, 114 in two stages. In a first stage, the pumping transducers 104 are configured to move liquid from the first reservoir 102 to the second reservoir 112. In a second stage, the vaporizing transducer 114 is configured to vaporize the liquid in the second reservoir 112.

This multistage arrangement can provide several notable advantages. For one, the ability to produce a high-quality vapor using the vaporizing transducer 114 can be dependent on the fluid height (or depth) of the liquid being vaporized. Accordingly, it can be important to maintain a constant fluid height within the second reservoir 112. To accomplish this, as liquid within the second reservoir 112 is vaporized (diminishing the amount of fluid within the second reservoir 112) the vaporized liquid must be replaced. The first reservoir 102 can hold bulk liquid that can be used to replace the vaporized liquid in the second reservoir 112. The pumping transducers 104 can be used to move the liquid from the first reservoir 102 to the second reservoir 112.

Another advantage associated with the multistage vaporizer 100 is that the movement of fluid from the first reservoir 102 to the second reservoir can be accomplished in a mechanically simple fashion, for example, without requiring any conventional pumps. Rather, the multistage vaporizer 100 uses transducers for both vaporization (with the vaporizing transducer 114) and pumping or movement of the liquid from the first reservoir 102 to the second reservoir 112 (with the pumping transducer 104).

In the illustrated embodiment, the first reservoir 102 and the second reservoir 112 are positioned in a "stacked" arrangement, with the second reservoir 112 positioned above the first reservoir 112. Accordingly, the first reservoir 102 can be considered a lower reservoir, and the second reservoir 112 can be considered an upper reservoir. This arrangement may be advantageous as it can minimize the overall size of the multistage vaporizer 100.

As shown in FIGS. 1B and 1C, the first reservoir 102 may comprise a bowl shape configured to hold a liquid. The first reservoir 102 may be formed by the base 101 or a portion of the base 101. As noted previously, the first reservoir 102 is configured for bulk storage of the liquid to be vaporized. Accordingly, the size of the first reservoir 102 can be configured based on a desired amount of liquid to be stored.

In the illustrated embodiment, the pumping transducer 104 are positioned within the first reservoir 102. For example, on a bottom surface of the first reservoir 102 or the base 101. While one pumping transducer 104 is illustrated, other numbers of pumping transducers 104 can be used, such as two, three, four or more pumping transducers 104. The pumping transducers 104 can comprise, for example, piezoelectric or ultrasonic transducers comprising vibrating diaphragms. In some instances, the pumping transducer 104 comprises a pumping crystal. The pumping transducer 104 can be configured to vibrate a frequency configured to generate relatively large droplets or a stream of the liquid in the first reservoir 102 and "throw" those droplets or stream in an upward direction. The vibrational frequency of the pumping transducers 104 can be adjusted to generate and throw the droplets or stream. In some embodiments, the transducers 104 (and/or the vaporizing transducer(s) 114) are configured to vibrate at between 1 MHz and 5 MHz, or between 1.5 MHz and 3 MHz, or between 1.66 MHz and 2.5 MHz, although other ranges of frequencies may also be used. The frequencies used can be selected based on the liquid being vaporized as well as the stage of device. In some embodiments, the transducers 104 comprise ceramic discs with metal bonded to them that can be modulated by power causing the discs to move in and out. In general, any mechanical, electrical, electro-mechanical, or other system for causing the resonation of the diagram can be used.

As shown in FIGS. 1A-1C, the first reservoir 102 can be closed with the cover 106. In some embodiments, the cover 106 can be configured to collect the droplets of water thrown upward by the pumping transducer 104 and direct them into the second reservoir 112. In the illustrated embodiment, the cover 106 includes an upper sloped surface 108. Droplets thrown upwards by the pumping transducer 104 can collect on the sloped surface 108. The sloped surface 108 then directs the droplets towards the second reservoir 112. For example, in the illustrated embodiment, the sloped surface 108 of the cover 106 is angled or curved such that droplets move towards a drip ring 110 that is positioned over the second reservoir 112. The droplets can collect on the drip ring 110 until they ultimately fall down into the second reservoir 112.

Collection and movement of the droplets by the sloped surface 108 of the cover can be caused in part by the surface tension of the liquid. For example, as the droplets are thrown upwards by the pumping transducer 104, they come into contact with the sloped surface 108 of the cover 106 and adhere to it via surface tension. Once adhered to the sloped surface 108, the angle of the sloped surface causes the adhered droplets to move down the slope towards the drip ring 110. As the liquid collects at the drip ring 110, a sufficient amount builds up such that the weight of the liquid at the drip ring 110 overcomes the surface tension causing the liquid to drip down into the second reservoir 112. In some embodiments, the drip ring 110 extends downwardly into the liquid within the second reservoir 112 guiding the droplets down into the second reservoir 112.

In some embodiments, the pumping transducer 104 can be configured to move liquid from the first reservoir 102 to the second reservoir 112 directly. For example, in some embodiments, the pumping transducer 104 can be tuned to produce droplets or a stream of liquid that moves directly into the second reservoir 112 without collecting on the sloped surface 108 of the cover 106.

As shown in FIGS. 1B and 1C, the second reservoir 112 may comprise a bowl shape configured to hold a liquid. A vaporizing transducer 114 is positioned within the second reservoir 112 and configured to vaporize the liquid. Accordingly, the second reservoir 112 may be considered a vaporizing reservoir. The vaporizing transducer 114 may comprise, for example, a piezoelectric or ultrasonic transducer comprising a vibrating diaphragm. In some instances, the vaporizing transducer 114 comprises a vaporizing crystal. Although the illustrated embodiment includes a single vaporizing transducer 114, other numbers of vaporizing transducers (e.g., one, two, three, four, or more) can be used.

Notably, in some embodiments, the vaporizing transducer 114 may be the same type of transducer as the pumping transducer 104, but the vibrational frequencies of the vaporizing transducer 114 and the pumping transducer 104 can be tuned or set to achieve their different purposes. For example, the pumping transducer 104 can be used with a vibrational frequency configured to generate and throw the large droplets of liquid up to the sloped surface 108 or directly into the second reservoir 112, while the vaporizing transducer 114 can be used with a vibrational frequency configured to vaporize the liquid and produce a mist of fine particles. In some embodiments, the particles are about or less than about 50 microns, 25 microns, 20 microns, 15 microns, 12 microns, 10 microns, 8 microns, or 5 microns.

The second reservoir 112 can be configured in size and shape to optimize the production of a high-quality mist by, for example, maintaining a constant fluid height 118 (see FIG. 1C) over the vaporizing transducer 114. This can be accomplished, for example, by providing one or more clefts 116 in an outer wall of the second reservoir 112. The clefts 116 can be set such that the lowest position of the cleft 116 above the vaporizing transducer 114 matches the desired fluid height 118. In the illustrated embodiment, liquid can only fill the second reservoir 112 to the cleft 116. Excess liquid spills through the cleft 116 and back to the first reservoir 102. In this way, the constant fluid height 118 in the second reservoir 112 over the vaporizing transducer 114 is maintained. In some embodiments, the second reservoir 112 is configured such the fluid height 118 is about 15 mm, although other heights (e.g., 4, 6, 8, 10, 12, 14, 16, 18, or 20 mm) may also be used. In preferred embodiments, the fluid height 118 is set so as to produce a high-quality mist of fine and consistently sized particles.

As shown in FIGS. 1B and 1C, in some embodiments, the drip ring 110 can extend downwardly from the cover 106 to a position that is below the cleft 116. In this configuration, a lower portion of the drip ring 110 is submerged within the liquid in the second reservoir 112. This configuration may be advantageous in that the drip ring 110 provides a mote wall that provides a barrier between the position at which droplets fall from the cover 106 or directly from the pumping transducer 104 down into the second reservoir 112 and the portion of the liquid directly above the vaporizing transducer 114. This can minimize surface wake, ripple, or other disturbance caused by the droplets falling into the second reservoir 112, which can advantageously further facilitate production of a high-quality vapor by minimizing surface disturbances in the liquid over the vaporizing transducer.

As shown in FIGS. 1A-1C (as well as FIGS. 3A and 3B, which are described below) the vapor exhaust 120 can be configured to allow the vapor generated by the vaporizing transducer 114 to exit the multistage vaporizer 100. Additionally, FIGS. 1A-1C and 3A-3B illustrate that the multistage vaporizer 100 can include an airway inlet 121. During use, the airway inlet 121 can be connected to or an airway (see FIGS. 3A and 3B) to deliver a gas into the multistage vaporizer 100. The airway inlet 121 directs the gas through a channel 123 formed to a venturi type chimney 125 that draws the vapor generated by the vaporizing transducer up and out the vapor exhaust 120. Additionally, fluid return holes 119 can be provided to allow liquid or large droplets to fall back into the second reservoir 112. This can help prevent large vapor droplets from exiting the vapor exhaust 120, helping to maintain a consistent vapor droplet size.

Figure 4:
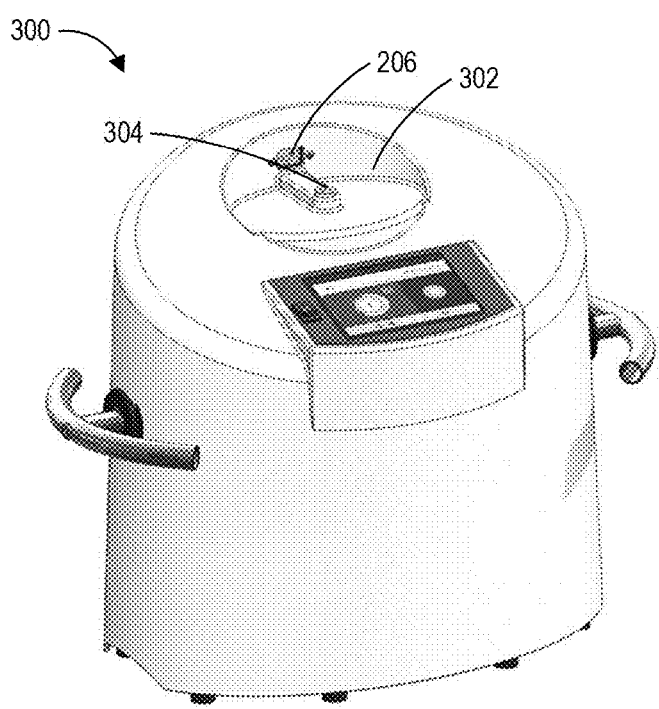
FIG. 4 illustrates an embodiment of a portion of a medical treatment system that is configured to receive the multistage vaporizer of FIG. 1A.

As shown, for example, in FIG. 1B, the multistage vaporizer can include electrical connections 137 configured to connect with corresponding electrical connections in a medical system 300, for example, as described below with reference to FIG. 4.

FIGS. 2A-2E illustrate various cross-sectional views of the multistage vaporizer 100 further illustrating positions of the various components according to the illustrated embodiment. FIG. 2A illustrates the multistage vaporizer 100 with the cover 106 removed from the base 101 to allow visualization of the interior region of the multistage vaporizer 100. FIG. 2B-2D illustrates an exploded view illustrating the base 101 (which forms the first reservoir 102), the pumping transducer 104, the second reservoir 112, and the cover 106. As shown in FIG. 2B, a threaded nub may be included on the base 102 and configured to engage with a threaded end of the second reservoir 112 to support, position, and connect the second reservoir 112 relative to the base 101. FIGS. 2C and 2D also illustrate a bracket 131 that can be configured to support the pumping transducer 104 relative to the base 101. FIG. 2E is a cross-sectional exploded view further illustrated the multistage vaporizer 100.

The multistage vaporizer 100 illustrated in FIGS. 1A-2E, however, can be modified in a variety of ways. For example, other form factors are possible. In some embodiments, the vapor exhaust 120 can be included on a side of the device rather than the top.

In some embodiments, the pumping transducer 104 and/or the vaporizing transducer 114 can be configured for fluid level detection and vaporization. Transducers, such as those used for the pumping transducers 104 and/or the vaporizing transducers 114, can be configured to generate ultrasonic waves within the fluid that can be detected to determine the depth of fluid. In some embodiments of the multi-stage vaporizer 100 the same transducers that provide pumping or vaporization can also be used for fluid level detection.

For example, in some embodiments, a transducer's vaporization function can be interrupted for a moment to generate an ultrasonic wave that is used to determine the fluid depth. As an example, vaporization can be interrupted for a few milliseconds to provide an interval in which the transducer can be used to determine fluid depth. Once fluid depth is determined, the transducer can return to its vaporization function. The fluid depth determination time step can be sufficiently short (e.g., a few milliseconds) such that vaporization performance is not substantially interrupted. In some embodiments, vaporization and fluid depth determination can be determined using the same frequency of the transducer. In some embodiments, the transducer can be configured to alternatingly vibrate at two frequencies: a first to vaporize the fluid (at which the transducer operates the majority of the time) and a second to provide a signal for fluid level detection (for a brief interval). The multistage vaporizer 100 can be configured to control operation based on the detected fluid levels. For example, fluid level detection within the second reservoir 112 can be used to prevent damage if there is too little fluid, and for the pumping transducers 104, it could be to report the reservoir fluid level and to prevent damage.

In some embodiments, the vaporizing transducer 104 can be configured to determine fluid density so as to determine the ideal energy to ultrasonically vaporize the fluid at an optimal frequency based on the fluid determined fluid density. For example, the vaporizing transducer 104 could generate an ultrasonic wave from which the speed of the signal as it goes thru the fluid can be used to determine the fluid density. This would allow optimization of the frequency to produce quality vapor for various liquids. In some instances, the fluid height must be known in order to determine the fluid density; however, in the illustrated embodiment, fluid height within the second reservoir is known based on the height of the clefts 116. By comparing the result to normal water, one can then make assumptions on the fluid and tune the system without the user having to enter any information about the fluid or concentration. In some embodiments, measured values can be compared to values stored in a look up table to optimize the system.

The speed at which sound travels through a liquid depends on the density of the liquid. So, by knowing the density of the fluid, one can determine the level (fluid height) based on the speed at which sound travels therethrough. Conversely, if one knows or can determine the level (fluid height), the fluid density can be determined, but there may be an input needed via the user.

In some embodiments, one or more of the transducers may be used to detect if the multistage vaporizer 100 is installed into a medical system 300 (see FIGS. 4-6B). For example, when installed, the transducer driver oscillates at the transducer's resonant frequency. When not connected, it does not.

Figure 3A:
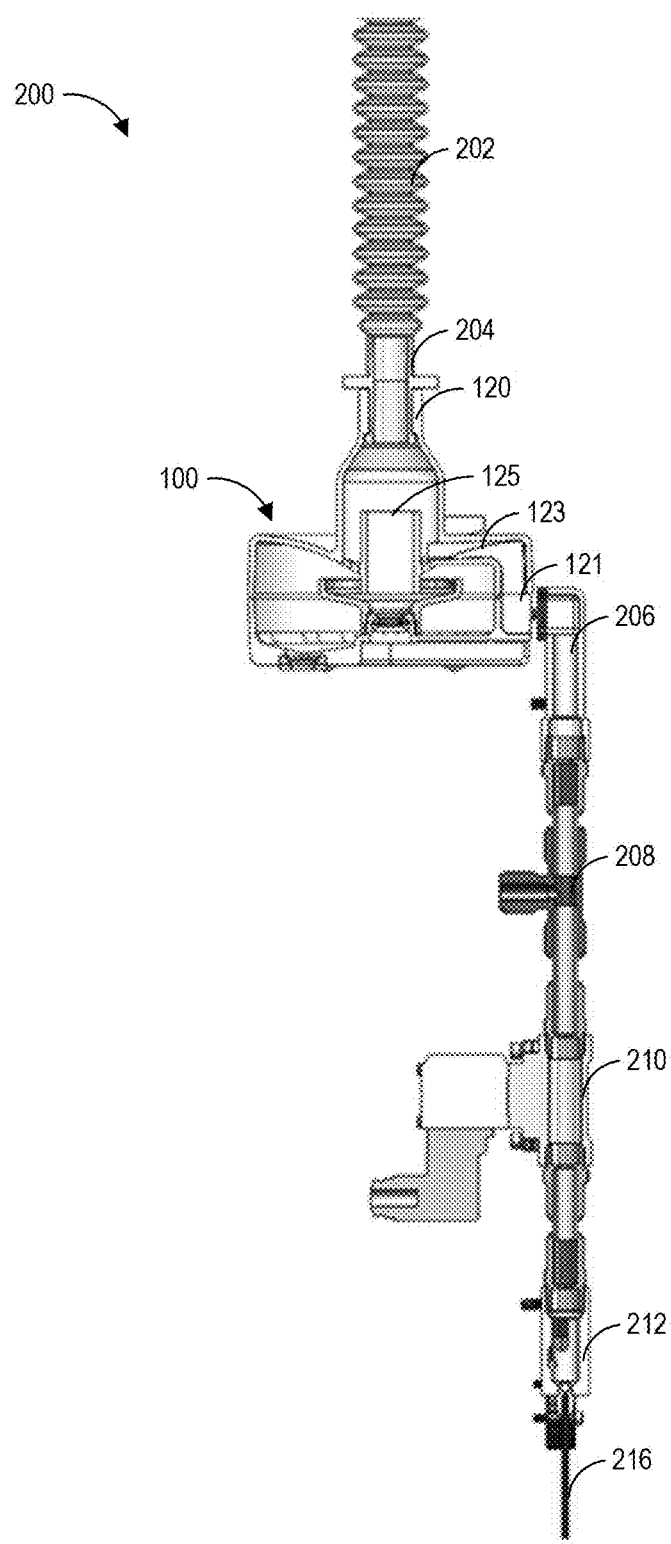
FIG. 3A is a cross-sectional view of an embodiment of an airway configured for use with a multistage vaporizer.
Figure 3B:
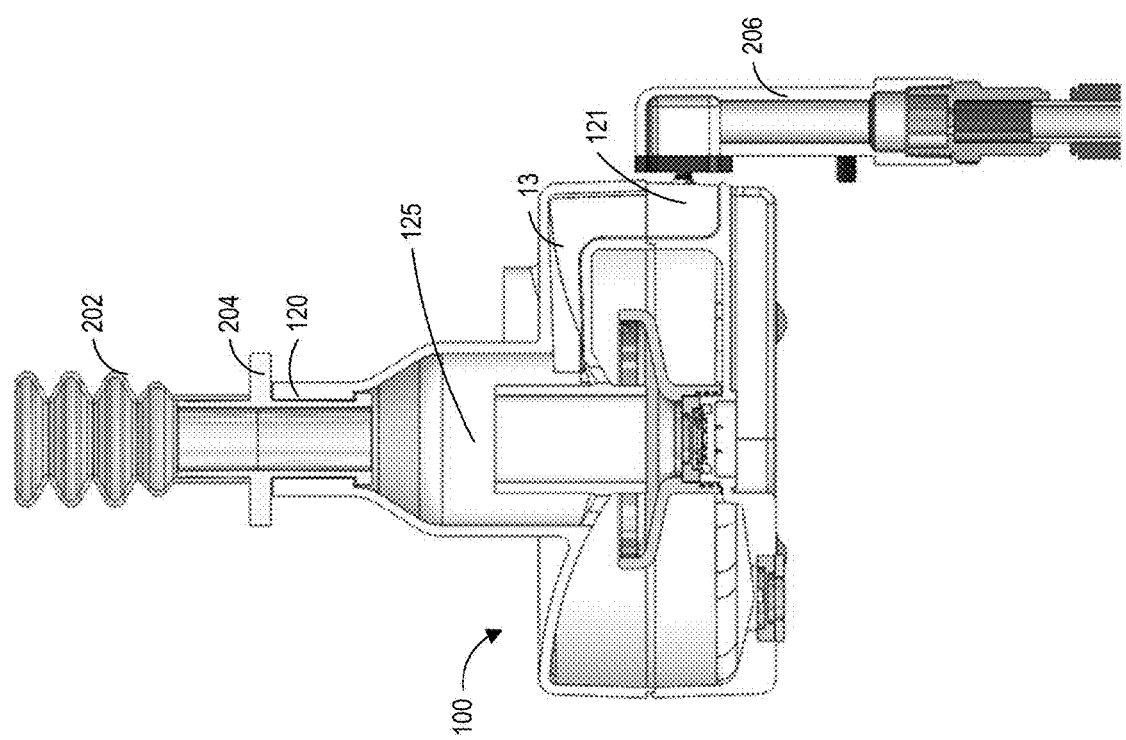
FIG. 3B is a cross-sectional view illustrating connections between the airway of FIG. 3A and the multistage vaporizer.
Figure 3D:
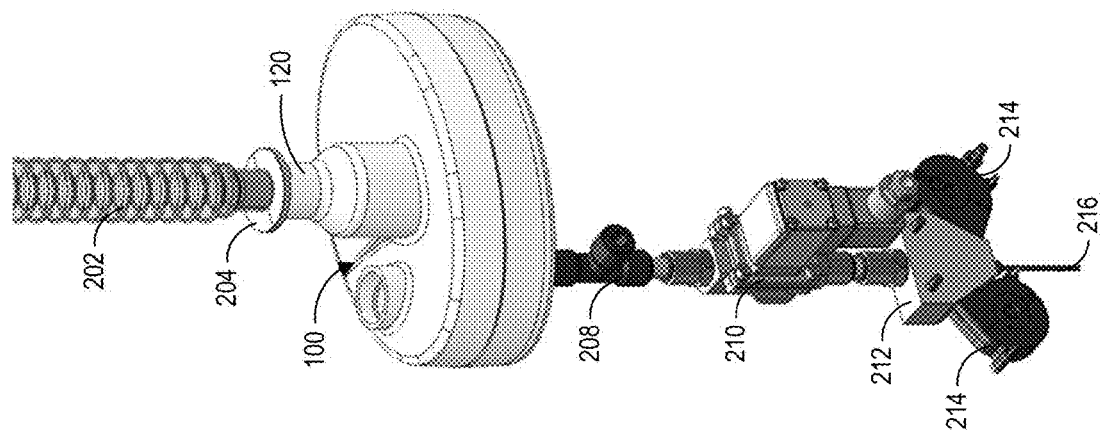
FIGS. 3C and 3D are back and front perspective views of the airway of FIG. 3A.
Figure 3C:
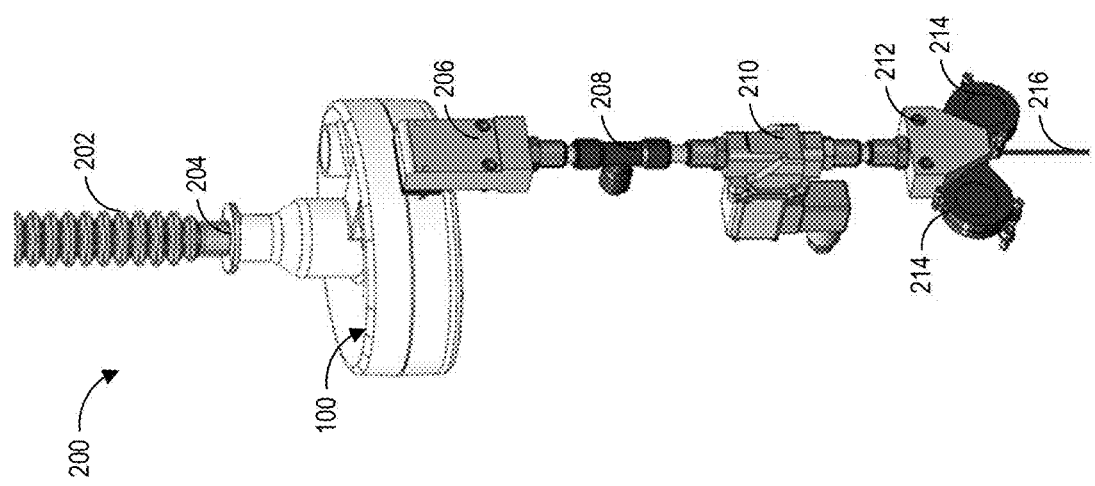

FIGS. 3A-3D illustrate an airway 200 configured for use with the multistage vaporizer 100. FIG. 3A is a cross-sectional view of the airway 200, FIG. 3B is a cross-sectional view illustrating connections between the airway 200 and the multistage vaporizer 100, and FIGS. 3C and 3D are back and front perspective views of the airway 200. As shown in FIGS. 3A-3D, the multistage vaporizer 100 may be connected to an airway 200. The airway 200 can direct gas (such as oxygen or air) through the multistage vaporizer 100. As the gas passes through the vaporizer 100 it can be mixed with the vaporized liquid generated by the multistage vaporizer 100.

In the illustrated embodiment, the airway 200 comprises a tube or hose 202 and a connector 204. The hose 202 can be configured to direct a mixture of gas and vapor from the multistage vaporizer 100 to a treatment site as shown in FIGS. 5A-6B. In some embodiments, the tube 202 is disposable. In the illustrated embodiment, the tube 202 is connected to the vapor exhaust 120 using the connector 204.

As illustrated in FIGS. 3A-3D, the pathway 200 may further include an air plenum 206, a tee 208, a blower isolation valve 210, a blower header 212, one or more blowers 214, and a drain line 216. Although a specific implementation is illustrated, other arrangements are comprising all, some, or different components are possible for the airway 200. In the illustrated embodiment, gas (such as oxygen or air) introduced into the airway 200 through the tee 208. Downstream of the tee 208, an air plenum 206 is connected to or positioned in proximity to the air inlet 121 of the multistage vaporize 100 so as to direct the gas into the vaporizer. Upstream of the tee 208, a blower isolation valve 210 may be provided. The blower isolation valve 210 can separate a blower assembly comprising a blower header 212 which is connected to one or more blowers 214. The blowers move the gas through airway 200, into the multistage vaporizer 100 where it is mixed with and picks up the vapor, and out through the hose 202. In the illustrated embodiment, a drain line 216 is also provided to allow drainage of any liquid that inadvertently enters the airway 200.

In some embodiments, the multistage vaporizer 100 can be integrated into a medical treatment system 300. FIG. 4 illustrates a portion of a medical treatment system 300 that can be used with the multistage vaporizer 100. In FIG. 4, the medical treatment system comprises a receptacle 302 configured to receive the multistage vaporizer. The receptacle 302 is connected to the air plenum 206 of the airway 200 such that when the multistage vaporize 200 is received in the receptacle 302 the air plenum 206 is aligned with the airway inlet of the multistage vaporizer 100. The receptacle 302 also include electrical connections 304 that are configured to connect with the multistage vaporizer 100 to control and communicated with the pumping and vaporizing transducers 104, 114. The electrical connections 304 can connect with the electrical connections 137 of the multistage vaporizer.

Figure 6A:
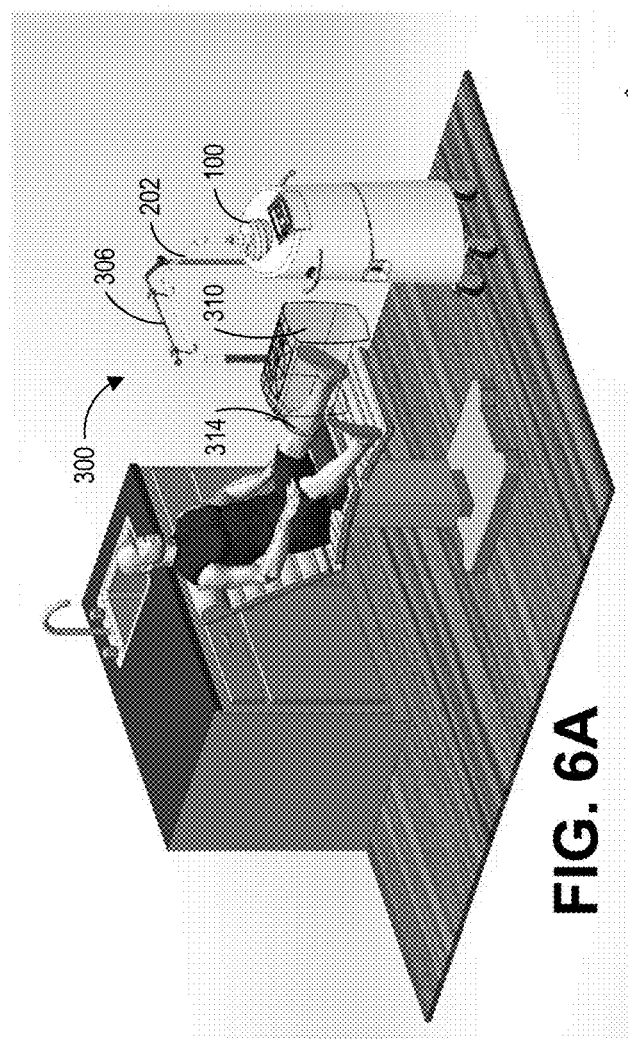
FIGS. 6A and 6B are front and back perspective views illustrating the medical treatment system of FIGS. 5A and 5B during use.
Figure 6B:
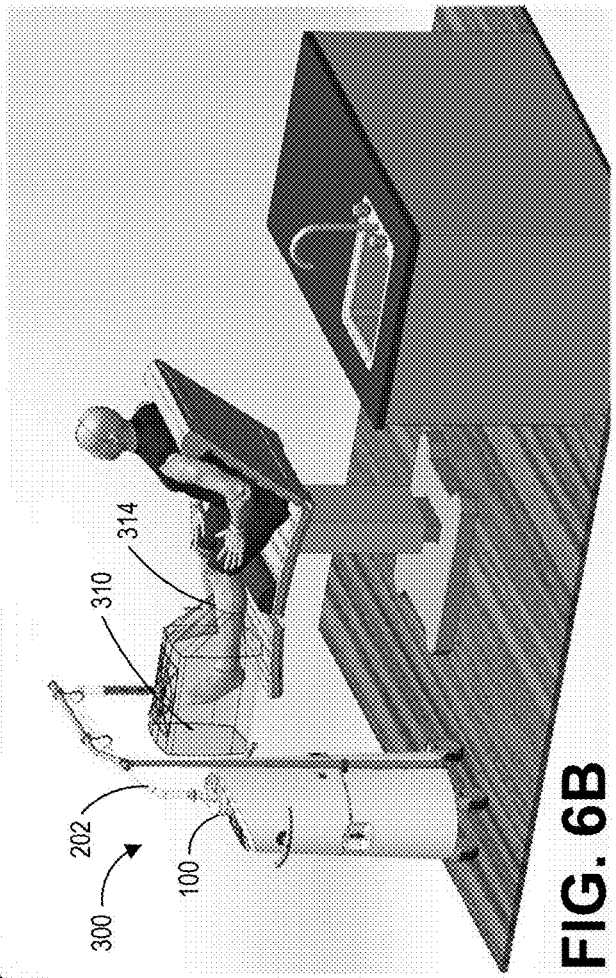

FIGS. 5A and 5B are front and back perspective views of the medical treatment system 300 including the multistage vaporizer 100. FIGS. 6A and 6B are perspective view illustrating an example of the medical treatment system 300 during use. In some embodiments, the system 300 is configured to generate a mist, which may contain a medicament, using the multistage vaporizer 100 and provide a medical treatment therewith. For example, as shown in FIG. 5A-6B, the mist generated by the vaporizer 100 can be directed into a disposable treatment chamber 310 configured to surround a portion of a patient's body for treatment. In the illustrated embodiment, the treatment chamber 310 is configured to surround a user's foot and lower leg. This can be done to treat diabetic foot ulcers, for example. FIGS. 5A-6B illustrate that gas and vapor can be directed by the house 202 into the treatment chamber 310. The hose 202 may be supported by a support structure or hanger 306. The hose 202 is connected to the treatment chamber 310 to direct the gas and vapor thereto. In the illustrated embodiment, the treatment chamber 310 comprises a frame 312 configured to help shape the treatment chamber 310. An opening 314 may be provided on the treatment chamber 310 through which a portion of the patient can be inserted. The opening 314 may be provided with a drawstring, elastic, or other structure configured to help maintain a seal around the patient.

In some embodiments, the systems described herein can include a remote management capability (IoT) that allows monitoring the health of the device and which can ensure that all treatments provided using the system are billed for.

In some embodiments, the vaporizer design described herein advantageously provides a clean solution that avoids spills. For example, the vaporizer can, in some embodiments, achieve these advantages via its top-mounted location and its easy-to-use fill port.

The foregoing description details certain embodiments of the multistage vaporizer devices and related systems and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the disclosure should not be taken to imply that the terminology is being re-defined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

The above description discloses several methods and materials of the present inventions. The inventions are susceptible to modifications in the methods and materials, as well as alterations in the fabrication methods and equipment. Such modifications will become apparent to those skilled in the art from a consideration of this disclosure or practice of the inventions disclosed herein. Consequently, it is not intended that the inventions be limited to the specific embodiments disclosed herein, but that the disclosure cover all modifications and alternatives coming within the true scope and spirit of the inventions as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties can be claimed through amendment of those claims or presentation of new claims in the present application or in a related application. Such amended or new claims, whether they are directed to the same invention or a different invention and whether they are different, broader, narrower, or equal in scope to the original claims, are to be considered within the subject matter of the inventions described herein.

What is claimed is:

1. A multistage vaporizer comprising:
a first reservoir configured to hold a liquid;
one or more pumping transducers positioned in the first reservoir;
a second reservoir positioned above the first reservoir;
a top cover having a sloped surface positioned over the first reservoir and the second reservoir; and
one or more vaporizing transducers positioned in the second reservoir,
wherein:
the one or more pumping transducers positioned in the first reservoir are configured to generate and move droplets of a liquid in the first reservoir upwards to adhere to the sloped surface,
the sloped surface is configured to direct the droplets of liquid towards a position over the second reservoir where the droplets of liquid fall into the second reservoir, and the one or more vaporizing transducers positioned in the second reservoir are configured to create a vapor of the liquid in the second reservoir.

2. The multistage vaporizer of claim 1, wherein the one or more pumping transducers and the one or more vaporizing transducers comprise piezoelectric or ultrasonic transducers comprising vibrating diaphragms.

3. The multistage vaporizer of claim 1, wherein the sloped surface collects the droplets of the liquid and based on surface tension deposits the droplets in the second reservoir.

4. The multistage vaporizer of claim 1, wherein the second reservoir comprises a wall having a specific height.

5. The multistage vaporizer of claim 4, wherein the wall includes a cleft to maintain a constant volume of liquid within the second reservoir.

6. The multistage vaporizer of claim 5, wherein the one or more vaporizing transducers and the specific height of the liquid allows for sensing of the liquid to determine fluid density and uses this with a formula/lookup table to further control vaporization.

7. The multistage vaporizer of claim 1, further comprising a mote wall extending downwardly from the sloped surface into the second reservoir and configured to reduce surface wake over the one or more vaporizing transducers.

8. A medical treatment system comprising:
the multistage vaporizer of claim 1; and
a treatment chamber adapted to receive a portion of a body of patient,
wherein vapor generated by the multistage vaporizer is directed into the treatment chamber.

9. The medical treatment system of claim 8, wherein the treatment chamber is adapted to receive at least a foot of the patient therein.

10. The medical treatment system of claim 8, wherein the treatment chamber is disposable.

11. A method comprising:
generating and moving droplets of a liquid upwards from a first reservoir to a sloped surface on a top cover using one or more pumping transducers positioned in the first reservoir,
directing droplets downward along the sloped surface to a position over a second reservoir;
dropping droplets downward from the position over the second reservoir into the second reservoir; and
generating a vapor of the liquid in the second reservoir using one or more vaporizing transducers positioned in the second reservoir.

12. The method of claim 11, wherein the one or more pumping transducers and the one or more vaporizing transducers comprise piezoelectric or ultrasonic transducers comprising vibrating diaphragms.

13. The method of claim 11, wherein generating and moving droplets of a liquid from a first reservoir to a second reservoir using one or more pumping transducers positioned in the first reservoir comprises vibrating the one or more pumping transducers at a first frequency.

14. The method of claim 13, wherein generating a vapor of the liquid in the second reservoir using one or more vaporizing transducers positioned in the second reservoir comprises vibrating the one or more vaporizing transducers at a second frequency, wherein the second frequency is different than the first frequency.

15. The method of claim 11, further comprising using the one or more vaporizing transducers and a specific height of the liquid allows to determine a fluid density of the liquid.

16. The method of claim 15, further comprising selecting one or more vaporization parameters based on the fluid density and a formula/lookup table to further control vaporization.

17. The method of claim 11, further comprising directing the vapor into a treatment chamber, wherein the treatment chamber is adapted to receive a portion of a body of a patient.

18. The method of claim 17, wherein the treatment chamber is adapted to receive at least a foot of the patient therein.

* * * * *